United States Patent [19]
Rens

[11] Patent Number: 6,114,396
[45] Date of Patent: Sep. 5, 2000

[54] STERILIZING OR DISINFECTING COMPOSITION

[75] Inventor: Brian Louis Rens, Kibler Park, South Africa

[73] Assignee: Optident International Ltd., Skipton, United Kingdom

[21] Appl. No.: 09/011,965

[22] PCT Filed: Jan. 31, 1996

[86] PCT No.: PCT/GB96/00206

§ 371 Date: Feb. 20, 1998

§ 102(e) Date: Feb. 20, 1998

[87] PCT Pub. No.: WO97/07679

PCT Pub. Date: Mar. 6, 1997

[30] Foreign Application Priority Data

Aug. 22, 1995 [GB] United Kingdom ............ 9517134

[51] Int. Cl.⁷ ..................................... A01N 33/08
[52] U.S. Cl. ............................................ 514/669
[58] Field of Search ............................. 514/669

[56] References Cited

U.S. PATENT DOCUMENTS 5,112,515  5/1992  Buxton et al. ................. 252/106

FOREIGN PATENT DOCUMENTS 0445924  9/1991  European Pat. Off. .

OTHER PUBLICATIONS

Abstract—Derwent Publications Ltd., London, GB, Section CH, Week 8426, AN 84–165127 "Carpet Shampoo Composition Contain Ammonia Ammonium Lauryl Sulphate Bromo Diol Di Chloro Benzyl Alcohol Antistatic Agent Nitro Propane".

Hawley's Chemical Dictionary, 11 Ed., Reinhold Co., NY, 1987, p. 448.

*Primary Examiner*—Jose' G. Dees
*Assistant Examiner*—Alton Pryor
*Attorney, Agent, or Firm*—Head, Johnson and Kachigian

[57] ABSTRACT

A chemical composition for a sterilizer of disinfectant comprising, 2-bromo-2-nitropropan-1,3-diol, a halogen, a halogen compound or a halogentated compound, which is preferably iodine and 2,4-dichlorobenzyl alcohol. Optionally other constituents may be included in the composition such as for example surfactants. Different embodiments of the invention may be used as a cold sterilizer, gloved and ungloved hand sprays and a scrub for use as a skin scrub.

35 Claims, No Drawings

STERILIZING OR DISINFECTING COMPOSITION

CROSS-REFERENCE TO RELATED APPLICATIONS

Priority is claimed to and this application relates to PCT Application No. GB96/00206 which claims priority from British Patent Application No. 9517134.4 filed Aug. 22, 1995.

This invention relates to a chemical composition suitable for use as a biocide.

A biocide is a composition which is able to destroy microorganisms. These can be divided into two, disinfectants which are agents that are able to destroy the germs of putrifaction or disease or inhibit their action and sterilizers which render objects aseptic, a condition where living pathogenic organisms are absent.

2,4-dichlorobenzyl alcohol is an antimicrobial agent which shows good activity against a wide range of yeasts, moulds dematophytic fungi and bacteria. It is known in the trade as Dybenal and is marketed by Boots PLC as Myacide SP.

2-bromo-2-nitropropan-1,3-diol is a widely used antibacterial agent which may be used as a preservative which is particularly useful as a means of preventing the proliferation of Gram-negative bacteria. It is known in the trade as BRONOPOL and is marketed by Boots PLC under the name of Bronopol-Boots or Myacide BT.

It has been used in a wide range of cosmetics, toiletries pharmaceuticals such as creams gels and ointments and household products such as fabric softeners and liquid detergents disinfectants and cleaners.

Tests have shown that 2-bromo-2-nitropropan-1,3-diol is not adversely affected by commonly used cationic, anionic or non-ionic surfactants.

2-bromo-2-nitropropan-1,3-diol is most stable in acid solution and is preferably used in slightly acidic compositions. It may however be used in neutral and mildly alkaline compositions. It is odour free and a non-irritant and has been shown to retain its activity in the presence of a range of other antimicrobial agents.

2-bromo-2-nitropropan-1,3-diol is bactericidal (causing death of bacteria) in a kill time of 24 hours at 37 C. at concentrations approximately 2–4 fold higher than bacteriostatic levels (inhibiting or retarding growth of bacteria). Tests to determine the bactericidal activity of 2-bromo-2-nitropropan-1,3-diol over short periods of time at room temperature (22 C.) indicate that it is more active against Gram-negative than Gram-positive bacteria. It has only limited activity against yeasts and fungi and hence it is known to use a combination of 2-bromo-2-nitropropan-1,3-diol and 2,4-dichlorobenzyl alcohol.

There is no evidence of antagonism to the action of 2-bromo-2-nitropropan-1,3-diol by 2,4-dichlorobenzyl alcohol and indeed 2-bromo-2-nitropropan-1,3-diol is microbiologically compatible with 2,4-dichlorobenzyl alcohol such that broard spectrum antimicrobial activity may be achieved with a combination of 2,4-dichlorobenzyl alcohol as anti-fungal agent and 2-bromo-2-nitropropan-1,3-diol as antibacterial agent.

The object of the invention is to provide a rapid acting biocide.

In the present invention there is provided a chemical composition for use as a sterilizer or disinfectant comprising 2-bromo-2-nitropropan-1,3-diol and 2,4-dichlorobenzyl alcohol and characterised in that the composition further comprises a halogen, a halogen compound or a halogenated compound.

In a preferred embodiment the halogen may comprise iodine.

In addition the composition may also comprise one or more surfactants. The or each surfactant may be a cationic, non-ionic, amphoteric or anionic surfactant. Preferably the anionic surfactant sodium lauryl sulphate is used.

The or each surfactant may be utilised in order to solubilise membrane proteins on the organisms thus decreasing the general kill time of the composition. The kill time of the composition can be defined as the time required for 99.9% biocidal action. Surfactants are of particular use when the composition is to be used on organisms having a waxy coat such as for example mycobacterium tuberculosis.

It is preferred that the composition is a water based composition but an alcohol such as 2-propanol (isopropyl alcohol) may additionally be included as a solvent as and when required.

To be a sterilizer the chemical composition must preferably meet the following criteria:-

It must exhibit complete spectrum biocidal action, have a kill time of less than 5 minutes with medically significant vegitative organisms and provide total prevention against the development of resistant strains of organisms to the composition.

In one embodiment of the present invention the composition of may be provided in the form of a concentrate for use as a cold sterilizer/disinfectant.

For such a cold sterilizer/disinfectant concentrate the concentration of 2-bromo-2-nitropropan-1,3-diol may be between 0.1 to 10.0% m/v and most preferably is about 2.5% m/v. The concentration of 2,4-dichlorobenzyl alcohol may be between 0.1 and 10% m/v and most preferably is about 1.0% m/v.

In the case of a cold sterilizer/disinfectant concentrate which utilises iodine as the halogen, iodine is preferably present in a range of 0.002 and 0.1% and is preferably in the order of 0.01% m/v It is to be understood that the upper values of the above ranges are approximate as the maximum concentration of each of the above constituents is dependent on toxicity levels.

Preferably the cold sterilizing composition further comprises sodium lauryl sulphate in a range of from 0.1 to 10.00% m/v and most preferably in the order of 3.0% m/v.

An example of the constituents of the concentrate of the present embodiment is given below:-

|  | % m/v |
|---|---|
| 2-bromo-2-nitropropan-1,3-diol | 2.5 |
| 2,4-dichlorobenzyl alcohol | 1.0 |
| Iodine | 0.01 |
| Sodium lauryl sulphate | 3.0 |
| 2-propanol | 65.0 |
| Water | UP TO 100% |

The concentrated composition is diluted for use by adding 5 parts of water to 1 part of the composition. Instruments to be sterilized are placed in the diluted solution. The recommended contact time is at least 2 minutes. In the case of laboratory spores and other highly resistant organisms however, contact times of in excess of 2 minutes are required. In practise however, the instruments are left in the composition until they are required for use.

In the case of iodine, Tests indicate that iodine may form a complex with either 2,4-dichlorbenzyl alcohol and/or 2-bromo-2-nitropropan-1,3-diol and the complex or complexes formed cause a significant decrease in kill time. The variation in concentration of iodine does not significantly change this decrease in the kill time as 0.0001% m/v iodine has been utilised at which level the iodine would have little or no biocidal effect alone but, however, this has had very little effect on the efficacy of the composition to bacteria.

The concept of complex formation is supported by the fact that when the iodine was substituted with povidone-iodine which is a polyvinylpyrrolidone-iodine complex, used as a topical anti-infective agent, which contains about 10% available iodine, the kill time of the composition was significantly greater than 5 minutes.

The composition has not in tests irritated the mucous membranes of subjects nor been the cause of any ulcerations.

Thus when instruments are removed from the sterilizing solution they may be used directly without the need to rinse the instruments beforehand. This in turn means that the possibility of the instruments being contaminated by organisms in the rinsing solution is eliminated.

Tests conducted by the South African Bureau of Standards on Stainless Steel (Grade BS 1449: part 2 of Grade 304 S15) have demonstrated that no staining or corrosion of stainless steel samples was detected after the stainless steel had been immersed in the sterilizer/disinfectant soution for a period of 8 hours at 80 C. This feature means that instruments which are being treated can be left in the sterilizer/disinfectant solution indefinately until required for use without adverse effects.

A modified composition containing a maximum of about 0.1 m/v 2-bromo-2-nitropropan-1,3-diol can be used as a skin disinfectant. The lower content of this active ingredient reduces the liklihood of skin irritablity and permits the modified composition to be applied directly to the skin.

Tests have shown that the bacterial efficacy of elemental iodine is higher than that of povidone-iodine and as such iodine is preferred.

The combination of a variety of other antimicrobial substances with iodine and optionally sodium lauryl sulphate has not provided a composition which meets the criteria indicated above for a sterilizing agent.

In a further embodiment there is provided a composition in accordance with the present application for use as a hand spray sterilizer/disinfectant which is designed for use with gloved hands.

Preferably in such a composition there is provided at least 0.08% w/v 2,4-dichlorobenzyl alcohol and at least 0.1% w/v 2-Bromo-2-nitropropan-1,3-diol. It is to be noted that the upper limit of both of these constituents may be determined by legal/safety/toxicological requirements.

Typically however the composition for use with gloved hands may comprise:-

|  | % m/v |
| --- | --- |
| 2-bromo-2-nitropropan-1,3-diol | 0.1 |
| 2,4-dichlorobenzyl alcohol | 0.05 |
| Iodine | 0.01 |
| 2-propanol | 70.0 |
|  | (v/v) |
| Water | UP TO 100% |

Other additives such as dye may be added if required. In such cases these will be in very small amounts for example 0.001% m/v.

In the latter example the composition may be prepared by firstly dissolving the dichlorobenzyl alcohol in the isopropyl alcohol, followed by dissolving the iodine in the alcoholic solution. Once the iodine is completely dissolved the water is added prior to the addition of the 2-Bromo-2-nitropropan-1,3-diol. Finally, when required, an aqueous dye solution may be added to the composition.

In a still further embodiment there is provided a sterilizer/disinfectant hand spray the composition of which may comprise at least 0.08% w/v 2,4-dichlorobenzyl alcohol, at least 0.1% w/v 2-Bromo-2-nitropropan-1,3-diol and a minimum of 0.0001% m/v of iodine. It is to be noted that the upper limit of these constituents may be determined by legal/safety toxicological requirements.

In this embodiment the composition may also contain compounds such as isopropyl myristate and/or glycerine and/or a dye.

Typically, the composition of the present invention for the hand spray for ungloved hands may comprise the following:-

|  | % m/v |
| --- | --- |
| 2-bromo-2-nitropropan-1,3-diol | 0.1 |
| 2,4-dichlorobenzyl alcohol | 0.05 |
| Iodine | 0.01 |
| Isopropyl myristate | 0.5 |
|  | (v/v) |
| Glycerine | 0.5 |
|  | (v/v) |
| 2-propanol | 70.0 |
| Water | UP TO 100% |

Again a dye may be used to identify the sterilizing composition. Clearly it is preferred that the dye for each different composition of the present invention is distinctive from each other so that a person may easily distinguish between the different compositions.

In the latter case the composition may be prepared by firstly dissolving the dichlorobenzyl alcohol in propan-2-ol and then adding the iodine. Once the iodine is completely dissolved water is added to the solution and the 2-bromo-2-nitropropan-1,3-diol is dissolved therein. Finally glycerine and isopropyl myristate are added sequentially and the composition is stirred.

In a still further embodiment of the present invention there is provided a sterilizer/detergent scrub which is for use as a skin scrub for medical staff needing to clean themselves ie. "scrub up" prior to undertaking an operation and for cleaning the skin of patients prior to their undergoing an operation. It is necessary to ensure that skin in an area in which an incision is to be made during an operation is sterile before any incisions are made.

Preferably the sterilizer/disinfectant scrub may comprise between 0.1 and 2.5% m/v 2-bromo-2-nitropropan-1,3-diol and most preferably is about 0.5% m/v. The concentration of 2,4-dichlorobenzyl alcohol may be between 0.05 and 1.0% m/v and most preferably is about 0.1% m/v.

Preferably the scrub also contains a minimum of 0.0001% m/v iodine, more preferably there is provided between 0.01 and 0.02% m/v iodine and most preferably there is about 0.014% m/v iodine.

Any other additives in common usage for scrub compositions may be incorporated in the present composition these may include quaternary ammonium biocides, cationic surface active agents, for example the commercial product BAC 50 which comprises both of the above may be utilised. Emolients for example polydimethylsiloxanes such as Dimethicone 200 may also be provided.

Thickening agents such as Glucamates and in particular Glucamate DOE 120 may additionally be utilised in the scrub composition as may amphoteric surface active agents and stabilizers such as Miranol CM2 conc, isopropyl myristate, perfumes, dyes and where required citric acid.

Preferably the composition has a pH of about 5.5 and the pH may be adjusted to such a value by the addition of an appropriate acid or alkali. Citric acid is usually used.

Typically, the composition of the present invention for the scrub may comprise the following:-

|  | % m/v |
| --- | --- |
| 2-bromo-2-nitropropan-1,3-diol | 0.5 |
| 2,4-dichlorobenzyl alcohol | 0.1 |
| Iodine | 0.014 |
| Isopropyl myristate | 1.0 |
|  | (v/v) |
| BAC 50 | 20.0 |
|  | (v/v) |
| Glucamate DOE 120 | 4.0 |
| Dimethicone 200 | 0.2 |
| Miranol CM2 conc. | 4.0 |
|  | (v/v) |
| Perfume | 0.2 |
| Dye |  |
| 2-propanol |  |
| Water | UP TO 100% |

Citric acid is used to adjust the pH of the mixture to the required value.

The above composition may be prepared as follows:-

Firstly the 2,4-dichlorobenzyl alcohol is dissolved in 2-propanol, upon dissolving iodine crystals are added and dissolved in the alcohol solution.

In a second heated container is added BAC 50 and Glucamate DOE 120. The mixture is heated to 60 C. and stirred until all the Glucamate DOE 120 has dissolved. Upon dissolving the contents of the first and second containers are combined and Miranol CM2 conc is added to the combined mixture and stirred.

In a third stage the above mixture has water and the 2-Bromo-2-nitropropan-1,3-diol added to it and the mixture is stirred until the diol is dissolved. Isopropyl myristate is subsequently added to the mixture and dissolved.

Finally water is added to make the mixture up to the required volume and a dye and dimethicone are added.

In order to determine the biocidal activity of the compositions of the present invention there is now provided and example of the tests undertaken with respect to the compositions of the present invention:-

In a preferred embodiment there is provided a chemical composition formulated for use as a cold sterilizer/disin concentrate for sterilizing instruments contaminated by bacterial and fungicidal organisms. The composition is water based and in a concentrated form comprises the following constituents:-

|  | % m/v |
| --- | --- |
| 2-bromo-2-nitropropan-1,3-diol | 1.0 |
| 2,4-dichlorobenzyl alcohol | 2.5 |
| Iodine | 0.01 |
| Sodium lauryl sulphate | 3.0 |
| 2-propanol | 65.0 |
| Water | UP TO 100% |

The test described herebelow were all undertaken using a diluted form of the above concentrate. Dilution factor was one part composition with five parts water.

Usually compositions containing 2-bromo-2-nitropropan-1,3-diol are tested for bactericidal effect by injecting a sample of an aqueous suspension of known concentration of a test organism into an aqueous solution of 2-bromo-2-nitropropan-1,3-diol. Counts for bacteria are taken at set intervals by diluting a set volume of the test mixture into peptone water and plating 1 standard amounts of these solutions in nutrient agar. An inactivating agent may be used if appropriate. This may comprise cysteine hydrochloride.

However, in the present application any standard method for testing disinfectants may be utilised, however instead of using an inactivator such as cysteine hydrochloride and then re-plating to assess the numbers of viable organisms remaining, after the period of incubation the solution is vacuum filtered through a 0.2 micron filter. A saline solution containing about 10% propylene glycol of at least 20 times the volume of the test the solution is passed through the filter to remove any traces of residual disinfectant. The propylene glycol is utilised in order to dissolve dichlorobenzyl alcohol.

The filter disc is then aseptically removed and plated out to assess any remaining viable organisms.

The latter working-up processes are all carried out under laminar flow and the rinse solution is sterile.

The work up process can take as little as 2 minutes. It is important to note that an chromatographic test by for example High Pressure Liquid Chromatography (HPLC) may be carried out on the last part of the rinse solution to confirm that none of the disinfectant remains on the filter disc. Tests have shown that this is correct.

In the present case the following steps were taken to determine the results provided below:-

1) All Solutions were prepared as specified in the South African Bureau of Standards Standard Specification Test for Quaternary Ammonium Compound Disinfectants (SABS 636-1971). There is provided two bottles of a sterile skimmed milk and hard water solution wherein a 1 ml of sterile water is added to each bottle containing 97 ml of hard water at a pH value of 6.6.

Cultures for test suspensions were prepared by inoculating a nutrient agar slope from a stock of the culture and incubating it at approximately 37 C. for 24 hours. Fresh slopes are prepared daily and a subculture made on a day between the third day and the fifteenth day inclusive may be utilised in the test.

A test suspension was prepared by washing the bacterial growth resulting from a 24 hour incubation from a slope with 10 ml of sterile water. The suspension was shaken in an appropriate container with a few glass beads to remove clumps and then the suspension was diluted to the appropriate concentration eg. so that it contains 100,000 +/–10,000 organisms per ml. The test suspension was placed in a water bath at approximately 22 C. and the prepared suspension was utilised within 3 hours of its preparation.

A control solution comprises 1 ml of sterile water in one of the bottles of milk. The test solution comprises a solution of the test sample in sterile water of a predetermined concentration.

Once the control and test solutions have been prepared and before testing takes place, they are both placed in a water bath at 22 C. for approximately 30 mins.

Test Procedure 1 ml of test suspension was added to the test solution and 30 seconds later a further 1 ml of the test suspension was added to the control solution. Lids are placed on each bottles and they are shaken and replaced in the water bath. The samples are exposed to the organism for a predetermined time period eg. 5 mins.

Results

The efficacy of the diluted composition described above as a sterilizer has been tested. By way of example, test results for the organism Psuedomonas aeruginosa are shown herebelow bearing in mind that the control count was 3049:-

| CONTACT TIME | % KILL |
|---|---|
| 1) *Pseudomonas aeruginosa* with Skimmed milk | |
| 2 MIN | 99.9 |
| 5 MIN | 99.9 |
| 15 MIN | 99.9 |
| 30 MIN | 99.9 |
| 60 MIN | 99.9 |
| 2) *Pseudomonas aeruginosa* without Skimmed milk | |
| 2 MIN | 99.9 |
| 5 MIN | 99.9 |
| 15 MIN | 99.9 |
| 30 MIN | 99.9 |
| 60 MIN | 99.9 |

Similar tests were carried out to determine the efficacy of the sterilant with regard to the following organisms:-

*Staphylococcus epidermidis*—control count 2159

*Streptococcus mutans*—control count 3142

*Candida albicans*—control count 2480

*Mycobacterium chelonae*—control count 3206

*Escherichia coli*—control count 2200

*Staphylococcus aureus*—control count 2100

In each case the percentage kill was 99.9% for each of the intervals.

Test have also been carried out on the viruses NCD and IBD. In each case the virus was in contact with the composition for a period of 20 minutes and it was found that in each case the virus strain was totally inactivated. It is to be noted that the titration results of the NCD and IBD viruses used in the positive (virus) control was TCID 50>10 3 and TCID 50>10 2 respectively.

The present invention is directed to a chemical composition for use as a sterilizer or disinfectant comprising 2-bromo-2-nitropropan-1,3-diol, 2,4-dichlorobenzyl alcohol, and at least one of a halogen, a halogen compound and a halogenated compound.

What is claimed is:

1. A chemical composition for use as a sterilizer or disinfectant, cold sterilizer/disinfectant concentrate, skin disinfectant chemical, hand spray sterilizer/disinfectant, sterilizer/disinfectant scrub, and/or combinations thereof comprising 2-bromo-2-nitropropan-1,3-diol, 2,4-dichlorobenzyl alcohol, and an iodine compound.

2. The chemical composition according to claim 1 wherein said composition further comprises at least one cationic, non-ionic, amphoteric or anionic surfactant.

3. The chemical composition according to claim 2 wherein said surfactant is sodium lauryl sulphate.

4. The chemical composition according to claim 1 wherein the concentration of 2-bromo-2-nitropropan-1,3-diol is between 0.1 to 10.0% m/v.

5. The chemical composition according to claim 1 wherein the concentration of 2-bromo-2-nitropropan-1,3-diol is about 2.5% m/v.

6. The chemical composition according to claim 1 wherein the concentration of 2,4-dichlorobenzyl alcohol is between 0.1 and 10% m/v.

7. The chemical composition according to claim 1 wherein said composition contains a maximum of about 0.1 m/v 2-bromo-2-nitropropan-1,3-diol.

8. The chemical composition according to claim 1 wherein said composition contains at least 0.08% w/v 2,4-dichlorobenzyl alcohol.

9. The chemical composition according to claim 1 wherein said composition contains at least 0.1% w/v 2-bromo-2-nitropropan-1,3-diol.

10. The chemical composition according to claim 1 further including a dye.

11. A chemical composition for use as a sterilizer or disinfectant comprising 2-bromo-2-nitropropan-1,3-diol, 2,4-dichlorobenzyl alcohol, and at least one of a halogen, a halogen compound and a halogenated compound, wherein said halogen comprises iodine.

12. A chemical composition for use as a sterilizer or disinfectant, cold sterilizer/disinfectant concentrate skin disinfectant chemical, hand spray sterilizer/disinfectant, sterilizer/disinfectant scrub, and/or combinations thereof comprising 2-bromo-2-nitropropan-1,3-diol, 2,4-dichlorobenzyl alcohol, at least one of a halogen, a halogen compound and a halogenated compound, and an alcoholic solvent.

13. A chemical composition for use as a sterilizer or disinfectant comprising 2-bromo-2-nitropropan-1,3-diol, 2,4-dichlorobenzyl alcohol, and at least one of a halogen, a halogen compound and a halogenated compound, wherein said composition further includes an alcoholic solvent, and wherein said alcoholic solvent is 2-propanol (isopropyl alcohol).

14. A cold sterilizer/disinfectant concentrate composition comprising 2-bromo-2-nitropropan-1,3-diol, 2,4-dichlorobenzyl alcohol, and an iodine compound, wherein the concentration of 2-bromo-2-nitropropan-1,3-diol is about 1.0% m/v.

15. A cold sterilizer/disinfectant concentrate composition comprising 2-bromo-2-nitropropan-1,3-diol, 2,4-dichlorobenzyl alcohol, and at least one of a halogen, a halogen compound and a halogenated compound wherein said halogen comprises iodine, and wherein the concentration of iodine is in a range of about 0.002 and 0.1% m/v.

16. A cold sterilizer/disinfectant concentrate composition comprising 2-bromo-2-nitropropan-1,3-diol, 2,4-dichlorobenzyl alcohol, and at least one of a halogen, a halogen compound and a halogenated compound wherein said halogen comprises iodine, and wherein the concentration of iodine is about 0.01% m/v.

17. A cold sterilizer/disinfectant concentrate composition comprising 2-bromo-2-nitropropan-1,3-diol, 2,4-dichlorobenzyl alcohol, an iodine compound, and at least one cationic, non-ionic, amphoteric or anionic surfactant, wherein said surfactant is sodium lauryl sulphate, and wherein the concentration of sodium lauryl sulphate is in a range of from 0.1 to 10.00% m/v.

18. A cold sterilizer/disinfectant concentrate composition comprising 2-bromo-2-nitropropan-1,3-diol, 2,4-dichlorobenzyl alcohol, an iodine compound, and at least one cationic, non-ionic, amphoteric or anionic surfactant, wherein said surfactant is sodium lauryl sulphate, and wherein the concentration of sodium lauryl sulphate is about 3.0% m/v.

19. A cold sterilizer/disinfectant concentrate composition comprising 2-bromo-2-nitropropan-1,3-diol, 2,4-dichlorobenzyl alcohol, and at least one of a halogen, a halogen compound and a halogenated compound, wherein said composition comprises:

2-bromo-2-nitropropan-1,3-diol as 2.5% m/v;

2,4-dichlorobenzyl alcohol as 1.0% m/v;

iodine as 0.01% m/v;

sodium lauryl sulphate as 3.0% m/v;

2-propanol as 65.0% m/v; and water up to 100%.

20. The cold sterilizer/disinfectant concentrate composition according to claim 19 wherein said composition is diluted in water by up to 5 parts of water to one part of the concentrate composition.

21. A hand spray sterilizer/disinfectant composition for use with gloved or ungloved hands comprising 2-bromo-2-nitropropan-1,3-diol, 2,4-dichlorobenzyl alcohol, and at least one of a halogen, a halogen compound and a halogenated compound wherein the halogen comprises iodine, and wherein said composition includes at least 0.0001% m/v iodine.

22. A hand spray sterilizer/disinfectant composition for use with gloved hands comprising 2-bromo-2-nitropropan-1,3-diol, 2,4-dichlorobenzyl alcohol, and at least one of a halogen, a halogen compound and a halogenated compound, wherein said composition comprises:

2-bromo-2-nitropropan-1,3-diol as 0.1% m/v;

2,4-dichlorobenzyl alcohol as 0.05% m/v;

iodine as 0.01% m/v;

2-propanol as 70.0% m/v; and water up to 100% m/v.

23. A hand spray sterilizer/disinfectant composition for use with ungloved hands comprising 2-bromo-2-nitropropan-1,3-diol, 2,4-dichlorobenzyl alcohol, at least one of a halogen, a halogen compound and a halogenated compound, and including isopropyl myristate.

24. A hand spray sterilizer/disinfectant composition for use with ungloved hands comprising 2-bromo-2-nitropropan-1,3-diol, 2,4-dichlorobenzyl alcohol, at least one of a halogen, a halogen compound and a halogenated compound, and including glycerine.

25. A hand spray sterilizer/disinfectant composition for use with ungloved hands comprising 2-bromo-2-nitropropan-1,3-diol, 2,4-dichlorobenzyl alcohol, and at least one of a halogen, a halogen compound and a halogenated compound, wherein said composition comprises:

2-bromo-2-nitropropan-1,3-diol as 0.1% m/v;

2,4-dichlorobenzyl alcohol as 0.05% m/v;

iodine as 0.01% m/v;

isopropyl myristate as 0.5% v/v;

glycerine as 0.5% v/v;

2-propanol as 70.0% m/v; and water up to 100% m/v.

26. A sterilizer/disinfectant scrub composition for use as a skin scrub comprising 2-bromo-2-nitropropan-1,3-diol, 2,4-dichlorobenzyl alcohol, and an iodine compound, wherein said composition includes about 0.1% and 2.5 m/v 2-bromo-2-nitropropan-1,3-diol.

27. A sterilizer/disinfectant scrub composition for use as a skin scrub comprising 2-bromo-2-nitropropan-1,3-diol, 2,4-dichlorobenzyl alcohol, and an iodine compound, wherein said composition includes about 0.5% m/v 2-bromo-2-nitropropan-1,3-diol.

28. A sterilizer/disinfectant scrub composition for use as a skin scrub comprising 2-bromo-2-nitropropan-1,3-diol, 2,4-dichlorobenzyl alcohol, and an iodine compound, wherein said composition includes between 0.05 and 1.0% m/v 2,4-dichlorobenzyl alcohol.

29. A sterilizer/disinfectant scrub composition for use as a skin scrub comprising 2-bromo-2-nitropropan-1,3-diol, 2,4-dichlorobenzyl alcohol, and an iodine compound, wherein said composition includes about 0.1% m/v 2,4-dichlorobenzyl alcohol.

30. A sterilizer/disinfectant scrub composition for use as a skin scrub comprising 2-bromo-2-nitropropan-1,3-diol, 2,4-dichlorobenzyl alcohol, and at least one of a halogen, a halogen compound and a halogenated compound, wherein the halogen comprises iodine, and wherein said composition includes a minimum of 0.0001% m/v iodine.

31. A sterilizer/disinfectant scrub composition for use as a skin scrub comprising 2-bromo-2-nitropropan-1,3-diol, 2,4-dichlorobenzyl alcohol, and at least one of a halogen, a halogen compound and a halogenated compound, wherein the halogen comprises iodine, and wherein said composition includes between 0.01 and 0.02% m/v iodine.

32. A sterilizer/disinfectant scrub composition for use as a skin scrub comprising 2-bromo-2-nitropropan-1,3-diol, 2,4-dichlorobenzyl alcohol, and at least one of a halogen, a halogen compound and a halogenated compound, wherein the halogen comprises iodine, and wherein said composition includes between about 0.014% m/v iodine.

33. A sterilizer/disinfectant scrub composition for use as a skin scrub comprising 2-bromo-2-nitropropan-1,3-diol, 2,4-dichlorobenzyl alcohol, and at least one of a halogen, a halogen compound and a halogenated compound wherein the halogen comprises iodine compound and wherein pH of the composition is about 5.5.

34. A sterilizer/disinfectant scrub composition for use as a skin scrub comprising 2-bromo-2-nitropropan-1,3-diol, 2,4-dichlorobenzyl alcohol, quaternary ammonium biocide, at least one of a halogen, a halogen compound and a halogenated compound and at least one cationic surface active agent, emollient, thickening agent, amphoteric surface active agent, stabilizer, isopropyl myristate, perfume, and dye.

35. A sterilizer/disinfectant scrub composition for use as a skin scrub comprising 2-bromo-2-nitropropan-1,3-diol, 2,4-dichlorobenzyl alcohol, isopropyl myristate, at least one of a halogen, a halogen compound and a halogenated compound and at least one cationic surface active agent, emollient, thickening agent, amphoteric surface active agent, stabilizer, quaternary ammonium biocide, perfume, and dye.

* * * * *